United States Patent [19]
Trojnar et al.

[11] Patent Number: 5,981,170
[45] Date of Patent: Nov. 9, 1999

[54] PEPTIDES, ARTIFICIAL ANTIGENS AND IMMUNOASSAY KITS

[75] Inventors: Jerzy Trojnar, Vintrie; Britta Wahren, Djursholm; Ulla Rudén, Sollentuna, all of Sweden

[73] Assignee: Ferring AB, Malmo, Sweden

[21] Appl. No.: 07/473,994

[22] PCT Filed: Oct. 27, 1988

[86] PCT No.: PCT/SE88/00570

§ 371 Date: Jun. 22, 1990

§ 102(e) Date: Jun. 22, 1990

[87] PCT Pub. No.: WO89/03844

PCT Pub. Date: May 5, 1989

[30] Foreign Application Priority Data

Oct. 28, 1987 [SE] Sweden ............................. 8704185-1

[51] Int. Cl.$^6$ .............................. C12Q 1/70; C07K 7/06; C07K 7/08; C07K 14/16
[52] U.S. Cl. .................................. 435/5; 514/12; 514/13; 514/14; 514/15; 514/16; 530/324; 530/325; 530/326; 530/327; 530/328; 530/329
[58] Field of Search ............................. 435/5, 7; 514/16, 514/15, 14, 13, 12; 530/329, 328, 327, 326, 325, 324

[56] References Cited

U.S. PATENT DOCUMENTS

| 4,629,783 | 12/1986 | Casand ..................................... 530/324 |
| 4,735,896 | 4/1988 | Wang et al. ................................. 435/5 |
| 4,812,556 | 3/1989 | Vahlne et al. ............................ 530/324 |
| 4,879,212 | 11/1989 | Wang et al. ................................. 435/5 |
| 4,957,737 | 9/1990 | Heimer ...................................... 424/88 |
| 5,001,049 | 3/1991 | Klein et al. ................................. 435/5 |

FOREIGN PATENT DOCUMENTS

| 0214709 | 3/1987 | European Pat. Off. . |
| 0219106 | 4/1987 | European Pat. Off. .................... 435/7 |
| 0247557 | 12/1987 | European Pat. Off. . |
| 8606414 | 11/1986 | WIPO . |
| 8706005 | 10/1987 | WIPO . |

OTHER PUBLICATIONS

Ratner, L., et al., *Nature*, 313: 275–283, Jan. 1985.
Gnann, J., et al., *J. of Infectious Diseases,* 156(2): 261–267, Aug. 1987.
Gnann, J. et al.,*J. of Virology,* 61(8): 2639–2641, Aug. 1987.
Gnann, J. et al., *Science,* 237: 1346–1349, Sep. 1987.
Journal of Virology, vol. 61, No. 8, Aug. 1987, p. 2639–2641, J.W. Gnann Jr. et al.: "Fine Mapping of an Immunodominant Domain in the Transmembrane Glyco–Protein of Human Immunodeficiency Virus".
Nature, vol. 329, Sep. 17, 1987, p. 248–250, E. Norrby et al: "Discrimination between antibodies to HIV and to Related Retroviruses Using Site–Directed Serology".
McDougal et al: "Binding of the Human Retrovirus HTLV–III/LAV/ARV/HIV to the CD4 (T4) Molecule: Conformation Dependence, Epitome Mapping, Antibody Inhibition, and Potential for Idiotypic Mimicry".
J. Gen. Virol. (1987), vol. 68, p. 2239–2244, G. Winkler et al: "Characterization of a Disulphide Bridge–Stabilized Antigenic Domain of Tick–Borne Encephalitis Virus Structural Glycoprotein".
Bretscher, *Febs Letters 85,* 145, 1978.
Ehrenberg, *Acta Chem Scand 43,* 177, 1989.
Janolino, *Archiv Biochem Biophys 258,* 265, 1987.
Hodges, *J. Biol. Chem. 256,* 1214, 1981.
Cann, *Archiv Biochem Biophys 221,* 57, 1983.
Paynovich, *Int. J. Pept. Prot. Res. 13,* 113, 1979.
Seiber, *Helv Chim Acta 59,* 1489, 1976.
Sisido, *Biopolymers 16,* 2723, 1977.
Gross, *The Peptides 3,* 146 and 161–162, 1981.

*Primary Examiner*—Robert D. Budens
*Attorney, Agent, or Firm*—Oblon, Spivak, McClelland, Maier & Neustadt, P.C.

[57] ABSTRACT

An artificial peptide having an amino acid sequence which corresponds to a naturally occurring amino acid sequence of a HIV comprising an epitope and which further has two cysteine residues located on each side of said epitope, and further having a sulphur bridge between said two cysteine residues, which has been formed by a chemical oxidation step, is described.

Furthermore, an artificial antigen which reacts with antibodies induced by a HIV is described. Said antigen mainly consists of an artificial peptide according to the invention.

Additionally, a method of detecting antibodies induced by a HIV in a sample of body fluid, wherein said sample is subjected to an immunoassay, especially ELISA, and wherein an artificial antigen according to the invention is used as a diagnostic antigen, is described. A diagnostic immunoassay kit for said method is also described.

Finally, a vaccine composition comprising, as an immunizing component, at least one antigen according to the invention, is described.

24 Claims, No Drawings

PEPTIDES, ARTIFICIAL ANTIGENS AND IMMUNOASSAY KITS

This application is a national stage application of international application PCT/SE88/00570, filed Oct. 27, 1988.

The present invention relates to artificial peptides having an amino acid sequence which corresponds to a naturally occurring amino acid sequence of a HIV comprising an epitope and which further has two cysteine residues located on each side of said epitope, and further having a sulphur bridge between said two cysteine residues which has been formed by a chemical oxidation step. The invention also relates to artificial antigens, which react with antibodies induced by a HIV, a method of detecting antibodies induced by a HIV in a sample of body fluid, a diagnostic immunoassay kit for said method, and a vaccine composition comprising, as an immunizing component, at least one antigen of the invention.

BACKGROUND AND PRIOR ART

The acquired immunodeficiency syndrome (AIDS) is a sexually transmitted disease that can also be transmitted through contaminated blood or blood products. It is caused by human immunodeficiency virus (HIV, previously called HTLV-III) which infects and is latently harboured in T4-lymphocytes and monocytes (Wong-Staal, F. and Gallo, R. C.: Human T-lymphotropic retroviruses. Nature 317:395–403, 1985). The chronically HIV-infected individual may in turn transmit HIV, most often by sexual contact. During infection, the immune response deteriorates and AIDS develops in 50–70% of the cases. The fate for the remainder of infected persons is not yet known. When AIDS develops it is lethal and characterised by opportunistic infection, Kaposi sarcoma, other tumors and/or neurological disease.

To diagnose an HIV infection, virus is isolated or the antibody response is measured. Virus isolation is successful in 30–50% of asymptomatic HIV infected persons, and in 90–100% of patients who developed AIDS. The antibody response is composed of immunoglobulins directed to the various structural and enzymatic components of HIV. They include the virus envelope proteins glycoprotein (gp)120, the transmembrane protein gp41 and their precursor gp160, the interior structural group antigens p24, 17 and 7/9 and their precursor p 55, the enzymes reverse transcriptase (RT) p65/51 and endonuclease p32 and protease. Antibodies to proteins of the regulatory regions of the HIV genome also develop. The correct identification of an HIV-infected person depends on the type(s) of immunoglobulin (Ig) he produces and on the correct composition of antigens used in the immunoassay.

One common way to establish a diagnosis through antibody detection is to screen serum samples by enzyme-linked immunosorbent assay (ELISA) (Sarngadharan, M. G., Popovic, M., Bruch, L., Schüpbach, J. and Gallo, R. C.: Antibodies reactive with human T-lymphotropic retroviruses (HTLV-III) in the serum of patients with AIDS. Science 224:506–508, 1984; Schüpbach, J., Haller, O., Vogt, M., Lüthy, R., Joller, H., Oelz, O., Popovic, M., Sarngadharan, M. G. and Gallo, R. C.: Antibodies to HTLV-III in Swiss patients with AIDS and pre-AIDS and in groups at risk for AIDS. The New Engl. J. Med. 312:265–270, 1985). Wells of microplates coated with viral antigens are reacted with the serum samples under investigation, washed, and antihuman Ig added. The latter reagent is labelled with an enzyme. After washing, the enzyme labelled antihuman Ig remains only if specific antiviral Ig was present in the serum sample. It is visualized by addition of a substrate for the enzyme and the color reaction quantified in a spectrophotometer. To verify this positive ELISA reaction, the serum sample is then added to e.g. Western blots which contain electrophoretically separated virus subcomponents. An immunoreaction on the Western blot will show whether Ig is reactive with the bands characteristic of viral subcomponents. Usually two different and characteristic bands are required to establish a definite diagnosis of HIV antibody.

The reliability of HIV antibody detection is dependent on the reagents of the ELISA plate. Lysates of infected cells may contain cellular contaminants, causing false positive serological reactions (Saag, M. S. and Britz, J.: Asymptomatic blood donor with a false positive HTLV-III western blot. The New Engl. J. Med. 314:118, 1985, Martin, P. W., Burger, D. R., Caouette, S. and Goldstein, A. S.: Importance of confirmatory tests after strongly positive HTLV-III screening tests. The New Engl. J. Med. 314:1577, 1986). Viral lysates usually have an over-representation of gag proteins and less envelope proteins which may cause false negative reactions. In addition to native viral lysates, recombinant-produced polypeptides have been produced (Ghrayeb, J., Kato. I., McKinney, S., Huang, J. J., Chanda, P. K., Ho. D. D., Sarngadharan, M. G., Chang, T. W. and Chang, N. T.: Human T-cell lymphotropic virus type III (HTLV-III) core antigens: synthesis in *Escherichia coli* and immunoreactivity with human sera. DNA 5:93–99, 1986; Chang, T. W., Kato, I., McKinney, S., Chanda, P., Barone, A. D., Wong-Staal, F., Gallo, R. C. and Chang, N. T.: Detection of antibodies to human T-cell lymphotropic virus-III (HTLV-III) with an immuno-assay employing a recombinant *Escheria coli*-derived viral antigenic peptide. Bio/Technology 3:905–909, 1985). The specificity and sensitivity of these assays are good, but not 100% (Chang, T. W. et al. ibid; Deinhardt, F., Eberle, J. and Gürtler, L.: Sensitivity and specificity of eight commercial and one recombinant anti-HIV ELISA tests. Lancet: 40, 1987).

The envelope protein gp120 varies between isolates (Wong-Staal, F. et al, ibid; Weiss, R. A., Clapham, P. R., Weber, J. N., Dalgleish, A. G., Lasky, L. A. and Berman, P. W.: Variable and conserved neutralization antigens of human immunodeficiency virus. Nature 324:572–575, 1986) and consequently peptides from them are not usually recommendable as ELISA antigens. Antibodies to gp41 have instead been considered the most sensitive diagnostic criterion of HIV infection (Sarngadharan, M. G., et al, ibid; Schüpbach, J., et al, ibid). gp41 contains regions that are well conserved between various isolates. Antibodies to p24 disappear with progressive disease (Lange, J. M. A., Paul, D. A., Huisman, H. G., de Wolf, F., van der Berg, H., Coutinho, R. A., Danner, S. A., van der Noordaa, J. and Goudsmit, J.: Persistent HIV antigenaemia and decline of HIV core antibodies associated with transition to AIDS. British. Med. J. 293:1459–1461, 1986) but are the ones which appear early. Regarding known antibody responses, a combination of measuring anti p24 and anti gp41 should therefore be the most reliable for all circumstances.

Performing Western blot is time consuming and expensive. To produce reliable antigens for use in ELISA seems preferable. No single assay has so far obtained 100% specificity and sensitivity (Deinhardt, F., et al, ibid; Lange, J. M. A., et al, ibid).

Recently, Gnann, J. W., et al (Journal of Virology, Aug. 1987, p. 2639–2641) identified a 12-amino-acid peptide derived from gp41 of HIV, that was recognized by 100% of the sera from HIV-infected sera. The described peptide contained two cystein residues, and the authors stated that they provide evidence that disulfide bond formation plays a key role in the antigenic conformation of the epitope. However, no such evidence was presented. The authors assumed that the peptide had cyclized spontaneously, and they attempted to prove it by reducing the alleged disulfide bond, but they failed. Instead they synthesized another 12-amino-acid peptide in which they had substituted serine for one of the cysteines, and when this was tested it reacted with only 2 of 22 HIV-positive test sera. The authors conclude that the presence of both cysteine residues is essential for the antigenic conformation of the epitope, possibly via formation of disulfide bonds. They have not proved that they had a disulfide bond in the investigated peptide, what they have done is to show that cysteine is better than serine in the specified position of said peptide. The existence of two cysteines in a peptide is not equivalent to a cyclic structure. The cyclization demands a defined chemical step, namely oxidation, and the result can be method dependent. If spontaneous cyclization occurs it is often incomplete and accompanied by polymerization.

In primary HIV disease, antibody tests may be negative during a period (Marlink, R. G., Allan, J. S., McLane, M. F., Essex, M., Anderson, K. C. and Groopman, J. E.: Low sensitivity of ELISA testing in early HIV Infection. The New Engl. J. Med. 315:1549, 1986).

The development of a single rapid, sensitive and specific assay for detecting antibodies to HIV, also at an early stage of infection, is most desirable.

DESCRIPTION OF THE INVENTION

The present invention provides i.a. a rapid, sensitive and specific assay for detection of antibodies induced by a HIV.

In one aspect of the invention there is provided an artificial peptide having an amino acid sequence which corresponds to a naturally occurring amino acid sequence of a HIV comprising an epitope and which further has two cysteine residues located on each side of said epitope, and further having a sulphur bridge between said two cysteine residues which has been formed by a chemical oxidation step. It is believed that this stabilization of the peptide by a sulphur bridge between two cysteine residues is responsible for the useful properties of the peptide, such as an enhancement of the antibody binding activity, as well as the chemical stability of the final product.

The artificial peptide includes at least two cysteine residues, which are cyclized to form a sulphur bridge. The two cysteine residues which are linked together may have one or more amino acid residues comprising an epitope between themselves, such as 2 to 10 residues, e.g. 5 residues. If the artificial peptide according to the invention includes more than two cysteine residues, still only one sulphur bridge between two cysteine residues is formed by a chemical oxidation step.

In a preferred embodiment of this aspect of the invention there is provided an artificial peptide, which is chosen from the group consisting of the peptide having the modified amino acid sequence

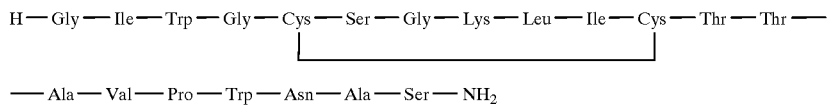

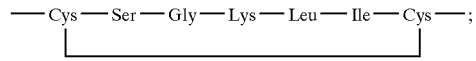

and peptides having a shorter sequence thereof including the modified sequence

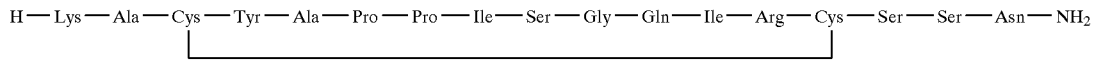

the peptide having the modified amino acid sequence and peptides having a shorter sequence thereof including the modified sequence

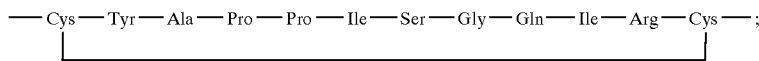

the peptide having the modified amino acid sequence

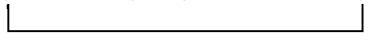

and the peptides having a shorter sequence thereof including the modified sequence

the peptide having the modified amino acid sequence

and peptides having a shorter sequence thereof including the modified sequence

the peptide having the modified amino acid sequence

and peptides having a shorter sequence thereof including the modified sequence

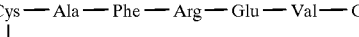

the peptide having the modified amino acid sequence

and peptides having a shorter sequence thereof including the modified sequence

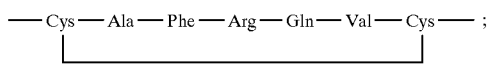

the peptide having the modified amino sequence

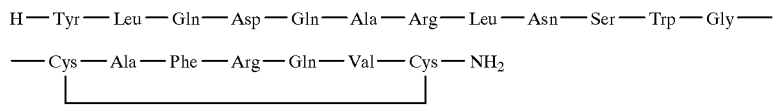

and peptides having a shorter sequence thereof including the modified sequence

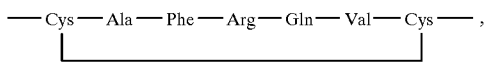

and the peptide having the modified amino acid sequence

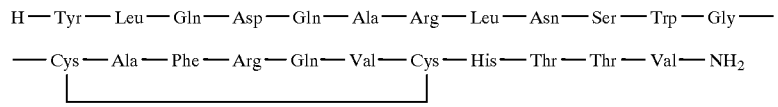

and peptides having a shorter sequence thereof including the modified sequence

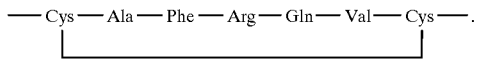

At present, the most preferred artificial peptide according to the invention is

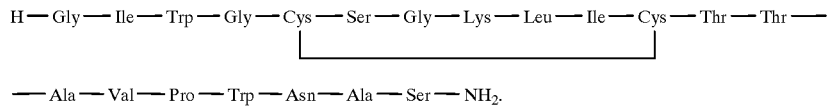

In another aspect of the invention there is provided an artificial antigen which reacts with antibodies induced by a HIV, which antigen mainly consists of an artificial peptide having an amino acid sequence which corresponds to a naturally occurring amino acid sequence of a HIV comprising an epitope and which further has two cysteine residues located on each side of said epitope, and further having a sulphur bridge between said two cysteine residues which has been formed by a chemical oxidation step.

In the specification and claims the expression "antigen mainly consists of an artificial peptide" indicates that the ability of the antigen to react with antibodies derives from the artificial peptide.

In a preferred embodiment of this aspect of the invention there is provided an artificial antigen which reacts with antibodies induced by a HIV, which antigen mainly consists of a preferred artificial peptide according to the invention, exemplified above.

The artificial antigens according to the invention can be immobilized or coupled to a carrier, such as mineral carriers, e.g. aluminium hydroxide, calcium phosphate, etc., plastic surfaces, e.g. microplates, beads, etc., proteins, such as bovine serum albumin or an immunizing component, such as keyhole limpet haemocyanin.

Even though the artificial antigens according to the invention so far only have been used as diagnostic antigens to detect antibodies induced by a HIV, in a sample of body fluid, it is believed that they can be used as immunizing components in vaccine compositions against a HIV. When a peptide (Example I) of the invention (without carrier) was injected into apes, antibodies directed against the C-terminal portion of the peptide were elicited.

Thus, a further aspect of the invention provides a vaccine composition, which comprises as an immunizing component, at least one antigen selected from artificial antigens according to the invention, together with a nontoxic pharmaceutically acceptable carrier and/or diluent.

In yet another aspect of the invention there is provided a method of detecting antibodies induced by a HIV in a sample of body fluid, wherein said sample is subjected to an immunoassay and an artificial antigen according to the invention is used as a diagnostic antigen. The sample of body fluid can be urine, saliva, tear fluid, milk, serum or blood.

The immunoassay in which the artificial antigens according to the invention can be used as diagnostic antigens is any immunoassay of choice, such as enzyme-linked immunosorbent assay (ELISA), radioimmunoassay (RIA), immunodiffusion or immunoelectrophoreses (IE).

In a preferred embodiment of this aspect of the invention ELISA is used as the immunoassay of choice.

In a further aspect of the invention there is provided a diagnostic immunoassay kit for the detection of antibodies induced by a HIV in a sample of body fluid, wherein an artificial antigen according to the invention is included as a diagnostic antigen. Depending on the immunoassay to be used, the kit will comprise other items, such as a positive standard serum sample, a negative standard serum sample, in the case of ELISA an enzyme conjugate and optionally a substrate for the enzyme conjugate, and also optionally buffer solution(s) and/or washing solution(s). Optionally all the reagents in the kit are contained in separate sealed test tubes or vials marked with specific labels.

Synthesis of the Artificial Peptides of the Invention

The artificial peptides of the invention can be produced by any known method of producing a linear peptide sequence, such as cloning, degradation, coupling of one amino acid residue to the next one in liquid phase or coupling the amino acids to one another starting with a solid phase (resin) to which the C-terminal of the first amino acid is coupled, whereupon the C-terminal of the next amino acid is coupled to the N-terminal of the first amino acid, etc., finally releasing the built-up peptide from the solid phase (so-called Merrifield synthesis). Once the appropriate linear peptide sequence is ready, it is subjected to a chemical oxidation step in order to cyclize two cysteine residues thereof, whereby a sulphur bridge is formed between the cysteine residues.

General Description of Synthesis

In the examples below, all peptides were synthesized on an Applied Biosystems 430A Peptide Synthesizer using a double coupling program with termination step after the second coupling. The resin used was of 4-methylbenzhydrylamine type with theoretical loading of 0.66 meq/g (Peptides International, Louisville, Ky., USA). The final product of the synthesis was dried in vacuo over night. After drying the peptide-resin was suspended in methanol (70 ml) and saturated with ammonia. The mixture was placed in pressurized steel vessel and left over night with magnetic stirring. The resin was then separated by filtration, washed several times with methanol and thoroughly dried in vacuo. The peptide was then cleaved from the resin by treatment with liquid hydrogen fluorid in the presence of anisole and ethyl-methyl-sulfide as scavengers (HF:anisole:EMS—10:05:05). After removal of hydrogen fluoride by evaporation the residue was suspended in ethyl acetate (100 ml) and filtered. The solid was washed on filter with additional ethyl acetate (3×100 ml) and the cleaved peptide extracted with acetic acid (100 ml). The extract was promptly diluted to the volume of 2 dm³ with 20% acetic acid in methanol and treated with 0.1 M solution of iodine in methanol until the faint brown colour persisted. Then the Dowex 1×8 ion exchanger in acetate form was added (3 g) (Bio-Rad, Richmond, Calif.) and the mixture was filtered. The filtrate was evaporated and the residue freeze-dried from 1% acetic acid in water. The product was then purified by reversed phase liquid chromatography on a column filled with Vydac 20–25μ (Separation Group, Calif.) in a suitable system containing acetonitrile in 0.1% trifluoroacetic acid water solution. The samples collected from the column were analyzed by analytical HPLC—Varian 5500 (Sunnyvale, Calif.) equipped with Bondapak C18 column (Millipore, Milford, Mass.). Fractions containing pure substance (>99.5%) were pooled, the solvent was evaporated and the product freeze-dried from 1% acetic acid in water. The final HPLC analysis was performed on ready product and the structure of the peptide was confirmed by amino acid analysis and FAB-MS (Fast atom bombardment spectrometry).

All amino acids used during the synthesis were protected with tert-butoxycarbonyl group at α-amino-function. The side chain protections used were as follows: Ser(BZL), Thr(BZL), Tyr(2-BrCbz), Lys(2-ClCbz), Orn(Cbz), Asp(BZL), Glu(BZL), Arg(Tos), Cys(Mob).

Amino acid derivatives were delivered by Bachem AG, Switzerland.

EXAMPLE I (The sequence corresponds to a sequence found in HIV-1-gp-41)

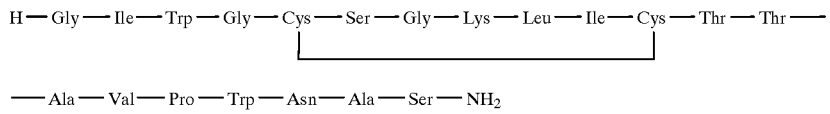

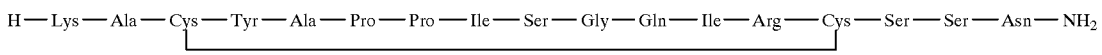

The peptide was prepared according to the general description of synthesis. Purity—99.9% according to HPLC (36% acetonitrile in 0.1% trifluoroacetic acid, retention time 6.79 min at 2 ml/min; detection at 223 nm).

The structure was confirmed by amino acid analysis and by FAB-MS.

EXAMPLE II (The sequence corresponds to a sequence found in HIV-1-gp120, modified by insertion of the cysteine residue located closer to the C-terminal.)

H—Lys—Ala—Cys—Tyr—Ala—Pro—Pro—Ile—Ser—Gly—Gln—Ile—Arg—Cys—Ser—Ser—Asn—NH₂

The peptide was prepared according to the general description of synthesis.

The structure was confirmed by amino acid analysis and by FAB-MS.

EXAMPLE III (The sequence corresponds to a sequence found in HIV-1-gp-41)

H—Ala—Val—Glu—Arg—Tyr—Leu—Lys—Asp—

—Gln—Gln—Leu—Leu—Gly—Ile—Trp—Gly—

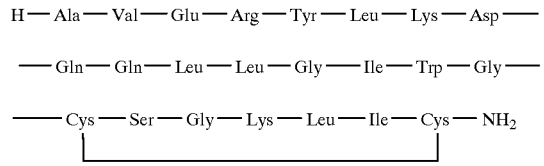

The peptide was prepared according to the general description of synthesis. The structure was confirmed by amino acid analysis and by FAB-MS.

EXAMPLE IV (The sequence corresponds to a sequence found in HIV-1-gp-41)

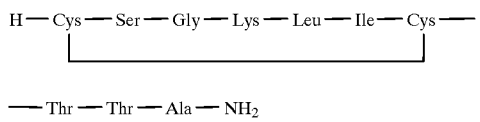

The peptide was prepared according to the general description of synthesis. The structure was confirmed by amino acid analysis and by FAB-MS.

EXAMPLE V (Reference)

(The sequence corresponds to a sequence found in HIV-1-gp-41)
H-Ser-Gly-Lys-Leu-Ile-Cys-Thr-Thr-Ala-Val-Pro-Trp-Asn-Ala-Ser-NH$_2$ The peptide was prepared according to the general description of synthesis, with the exception of the oxidation step with iodine.

Purity>98.5%(HPCL).

The structure was confirmed by amino acid analysis and by FAB-MS.

EXAMPLE VI (Reference)

(The sequence corresponds to a sequence found in HIV-1-gp-41)
H-Gly-Ile-Trp-Gly-Cys-Ser-Gly-Lys-Leu-Ile-Cys-Thr-Thr-Ala-Val-Pro-Trp-Asn-Ala-Ser-NH$_2$ The peptide was prepared according to the general description of synthesis, with the exception of the oxidation step with iodine.

The structure was confirmed by amino acid analysis and by FAB-MS.

EXAMPLE VII (The sequence corresponds to a sequence found in HIV-2-gp41)

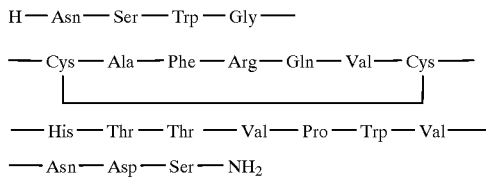

The peptide was prepared according to the general description of synthesis. The structure was confirmed by amino acid analysis and by FAB-MS.

EXAMPLE VIII (The sequence corresponds to a sequence found in HIV-2 transmembrane)

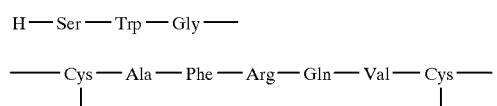

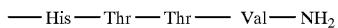

The peptide was prepared according to the general description of synthesis. The structure was confirmed by amino acid analysis and by FAB-MS.

EXAMPLE IX (The sequence corresponds to a sequence found in HIV-2 transmembrane)

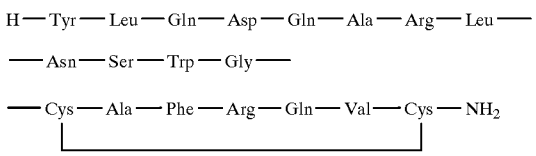

The peptide was prepared according to the general description of synthesis. The structure was confirmed by amino acid analysis and by FAB-MS.

EXAMPLE X (The sequence corresponds to a sequence found in HIV-2 transmembrane)

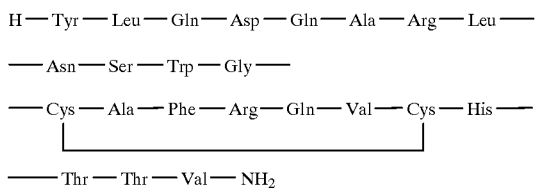

The peptide was prepared according to the general description of synthesis. The structure was confirmed by amino acid analysis and by FAB-MS.

Detection of Antibodies Induced by HIV in Blood Samples

For the detection of antiboides induced by HIV in blood samples use was made of ELISA. (Engvall, E. and Perlmann, P.: Enzyme-linked immunosorbent assay (ELISA). III Quantification of specific antibodies by enzyme labelled anti-immunoglobulin in antigen-coated tubes. J. Immunol. 109.129–135,1972).

Materials:
  Plates: Nunc 96 F, Roskilde, Denmark
  Conjugate: HRPO rabbit anti-human Ig, Dakopatts, Glostrup, Denmark
  Buffers: Carbonate buffer: 0.05 M sodium carbonate buffer, pH approx. 9.5.
    Buffer A: Phosphate buffered saline (PBS) without Ca$^{++}$ and Mg$^{++}$, and with 0.5% bovine serum albumin (BSA) and 0.05% Tween 20+20% fetal calf serum (FCS). Can be stored at 4° C. for 1–3 days.
    OPD buffer: 0.0347 M citric acid, 0.0667 M Na$_2$HPO$_4$, pH 5.5. Can be stored 1 month. OPD tablets, Dakopatts, Glostrup, Denmark.
    Washing solution: 0.9% NaCl with 0.05% Tween 20.

Methods:
  Coating: A solution of the coating antigen (test peptide), 5 µg to 20 µg per ml, is made in carbonate buffer. 100 µl of the solution is added to each well of stripes or of 96-well microplates. The adsorption takes place over night, 18 hrs, at room temperature. The coated plates can be stored with their contents in 4° C. until use.

Serum assay:

1. Empty and wash the plate 4 times with washing solution.
2. Add 100 μl of serum diluted 1:100 in buffer A.
3. Add 100 μl of just buffer A to one well; this well serves as a blank.
4. Incubate 60 min at 37° C. (Dilute the conjugate during this period, see 6).
5. Wash 4 times with washing solution. Empty.
6. Add 100 μl of a conjugate, e.g. HRPO rabbit anti-human IgG,IgA,IgM diluted 1:15 000 in buffer A (for instance 5 μl added to 0.75 ml, dilute this 1:100).
7. Incubate at 37° C. for 30 min. (Prepare substrate solution during this period, see 9).
8. Wash 4 times with washing solution. Empty.
9. Add 100 μl OPD substrate (6 tablets/10 ml OPD buffer. Use a clean vessel. 15–20 min are needed to dissolve the tablets. When dissolved, add 4 μl $H_2O_2$/10 ml).
10. Incubate 30 min at room temperature. Stop the reaction with 100 μl 2.5 M $H_2SO_4$.
11. Read plate at 490 nm. Negative values should be below 0.250.

Using the above described materials and methods the following materials were tested as diagnostic antigens (coating antigens) for the detection of antibodies induced by HIV in serum samples from infected patients:

A. A recombinant protein gp 160 (expressed in Baculovirus in insect cells). Received from Repligen Corp. Cambridge, Mass., USA.

B. A recombinant polypeptide p 121 (with conserved region of gp 41, cloned in *E. coli*) received from Repligen Corp. Cambridge, Mass., USA.

C. A synthetic peptide described in Example V (Reference) of this specification (only one cysteine residue, no cyclization).

D. An artificial peptide according to the invention described in Example I of this specification.

E. An artificial peptide according to the invention described in Example II of this specification.

Serum samples from HIV infected human patients and from non-infected humans were tested.

Their serological status had been confirmed by Western blot.

The results were as follows:

| | HIV antibody ELISA | | |
|---|---|---|---|
| Test material | Sensitivity (%) | Specificity (%) | Number of tested persons |
| A. | 97.7 | 100 | 95 |
| B. | 97.5 | 75 | 87 |
| C. | 93.9 | 90.7 | 370 |
| D. | 100 | 99.9 | 2225 |
| E. | 100 | 100 | 80 |

From the above results it is evident that the tested artificial peptides according to the invention (D. and E.) exhibits both excellent sensitivity and excellent specificity.

In the same way the following additional artificial peptides according to the invention were tested, namely F. An artificial peptide described in Example III of this specification, G. An artificial peptide described in Example IV of this specification, H. An artificial peptide described in Example VIII of this specification, I. An artificial peptide described in Example IX of this specification, and J. An artificial peptide described in Example X of this specification.

The results were as follows:

| | HIV antibody ELISA | | |
|---|---|---|---|
| Test material | Sensitivity (%) | Specificity (%) | Number of tested persons |
| F. | 92.1 | (100) | 50 |
| G. | 84.2 | (100) | 31 |
| H. | 100 | 98.7 | 180 |
| I. | 100 | 98.7 | 180 |
| J. | 100 | 90 | 21 |

Even though these peptides (F.–J.) are not as good as the peptides D. and E. they show a good reactivity with antibodies induced by HIV.

Comparison of Seroreactivity between a Cyclic and a Linear Peptide

Using the above described materials and methods (ELISA) the cyclic peptide of Example I and the corresponding linear peptide of Example VI were tested at different serum dilutions.

The results were as follows:

| | | HIV antibody ELISA | | | |
|---|---|---|---|---|---|
| Amount of peptide | Serum dilution | Number of positive reactions with peptide | | Number of serum dilutions having highest absorbancy values | |
| | | cyclic | linear | cyclic | linear |
| | | HIV seropositive, n = 66 | | | |
| 5 μg | 1/20 | 66 | 66 | | |
| | 1/100 | 61 | 60 | 118 | 78 |
| | 1/500 | 27 | 19 | | |
| | | 154 | 145 | | |
| 10 μg | 1/20 | 66 | 66 | | |
| | 1/100 | 65 | 61 | 166 | 30 |
| | 1/500 | 36 | 13 | | |
| | | 166 | 139 | | |
| 20 μg | 1/20 | 66 | 66 | | |
| | 1/100 | 58 | 59 | 129 | 67 |
| | 1/500 | 23 | 19 | | |
| | | 147 | 144 | | |
| Total number of reactions | | 467 | 428 | 413 | 175 |

-continued

HIV antibody ELISA

| Amount of peptide | Serum dilution | Number of positive reactions with peptide cyclic | Number of positive reactions with peptide linear | Number of serum dilutions having highest absorbancy values cyclic | Number of serum dilutions having highest absorbancy values linear |
|---|---|---|---|---|---|
| HIV seronegative, n = 22 | | | | | |
| 5 μg | 1/20 | 0 | 0 | 2 | 11 |
| 10 μg | 1/20 | 0 | 0 | 5 | 2 |
| 20 μg | 1/20 | 0 | 0 | 1 | 1 |
| Total number of reactions | | 0 | 0 | 8 | 14 |

The results of the above comparison illustrate the advantage of the cyclic peptide as compared to the corresponding linear peptide. Both peptides give positive results with all sera at the lowest serum dilution. However, the reactions decrease rapidly with the linear peptide, while the cyclic peptide is capable of keeping its configuration for positive antibody reactivity (see the above Table, columns 3 and 4). This is a necessary characteristic to be able to detect with certainty sera having low antibody titres.

A direct comparison of the absorbancy values in ELISA shows that the cyclic peptide is by far superior to the linear one (see the above Table, columns 5 and 6).

The relationship is the reverse when it comes to the antibody-negative sera. The specificity is 100% for both peptides, but the background values are higher for the linear peptide. This indicates advantages in both specific and non-specific reactions for the cyclic peptide.

We claim:

1. A diagnostic immunoassay kit for the detection of antibodies induced by a HIV in a sample of body fluid, comprising:

a peptide having a sulfur bridge between two cysteine residues formed by a chemical oxidation step, said peptide selected from the group consisting of

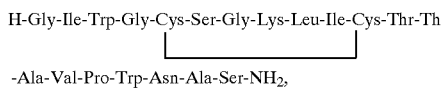

H-Gly-Ile-Trp-Gly-Cys-Ser-Gly-Lys-Leu-Ile-Cys-Thr-Th

-Ala-Val-Pro-Trp-Asn-Ala-Ser-NH$_2$,

2. A diagnostic immunoassay kit according to claim 1, characterized in that it additionally comprises a positive standard serum sample, a negative standard serum sample, an enzyme conjugate, optionally a substrate for the enzyme conjugate, and optionally buffer solution(s) and/or washing solutions.

3. A diagnostic immunoassay kit according to claim 1, wherein said peptide has been immobilized or coupled to a carrier.

4. A diagnostic immunoassay kit for the detection of antibodies induced by a HIV in a sample of body fluid, comprising:

a peptide having a sulfur bridge between two cysteine residues formed by a chemical oxidation step, said peptide selected from the group consisting of

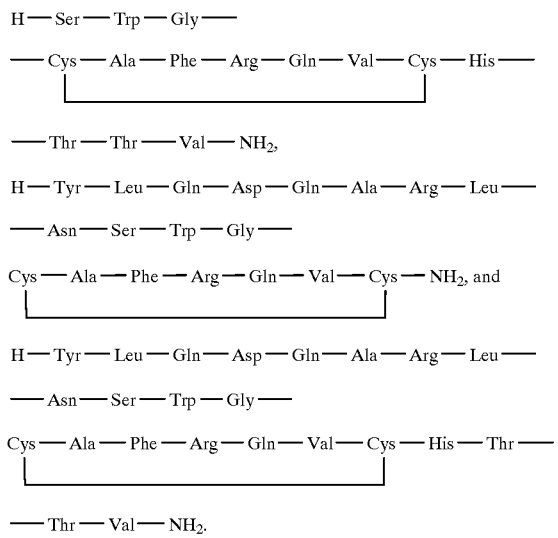

5. A diagnostic immunoassay kit according to claim 4, characterized in that it additionally comprises a positive standard serum sample, a negative standard serum sample, an enzyme conjugate, optionally a substrate for the enzyme conjugate, and optionally buffer solution(s) and/or washing solution(s).

6. A diagnostic immunoassay kit according to claim 4, wherein said peptide has been immobilized or coupled to a carrier.

7. An isolated and purified peptide having a sulfur bridge between two cysteine residues formed by a chemical oxidation step, said peptide selected from the group consisting of

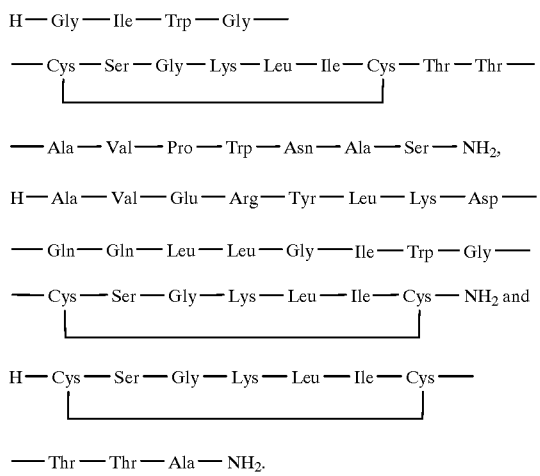

8. An antigen which specifically binds with antibodies induced by a HIV characterized in that the antigen was produced with an isolated and purified peptide having a sulfur bridge between two cysteine residues formed by a chemical oxidation step, said peptide selected from the group consisting of

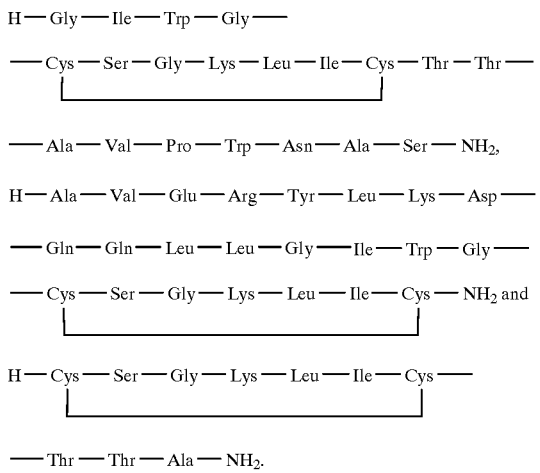

9. The antigen of claim 8, characterized in that it has been immobilized or coupled to a carrier.

10. A method of detecting antibodies induced by a HIV in a sample of body fluid, wherein said sample is subjected to an immunoassay, Characterized in that an antigen according to claim 8 or 9 is used as a diagnostic antigen.

11. A method according to claim 10, wherein said sample is subjected to enzyme-linked immunosorbant assay (ELISA) characterized in that said antigen is used as a diagnostic coating antigen.

12. An isolated and purified peptide having a sulfur bridge between two cysteine residues formed by a chemical oxidation step, said peptide selected from the group consisting of

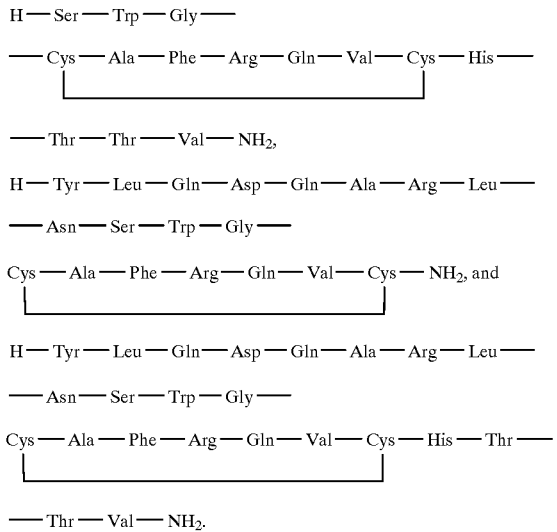

13. An antigen which specifically binds with antibodies induced by a HIV characterized in that the antigen was produced with an isolated and purified peptide having a sulfur bridge between two cysteine residues formed by a chemical oxidation step, said peptide selected from the group consisting of

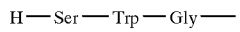

-continued

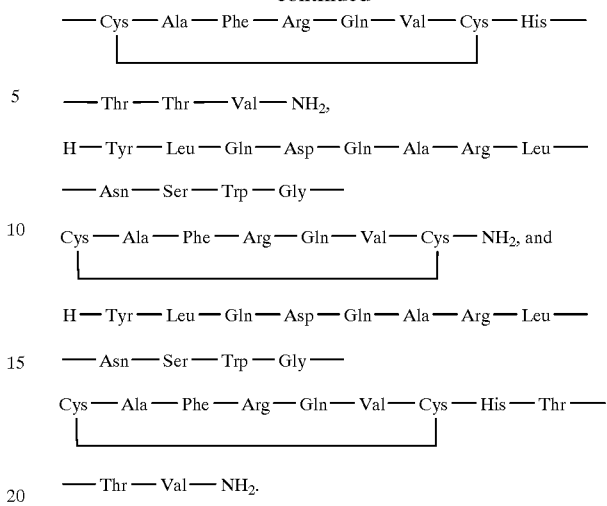

14. An antigen according to claim 13, characterized in that it has been immobilized or coupled to a carrier.

15. A method of detecting antibodies induced by a HIV in a sample of body fluid, wherein said sample is subjected to an immunoassay, characterized in that an antigen according to claims 13 or 14 is used as a diagnostic antigen.

16. A method according to claim 15, wherein said sample is subjected to enzyme-linked immunosorbant assay (ELISA) characterized in that said artificial antigen is used as a diagnostic coating antigen.

17. A diagnostic immunoassay kit for the detection of antibodies induced by a HIV in a sample of body fluid, comprising:

a peptide having a sulfur bridge between two cysteine residues formed by a chemical oxidation step, of formula:

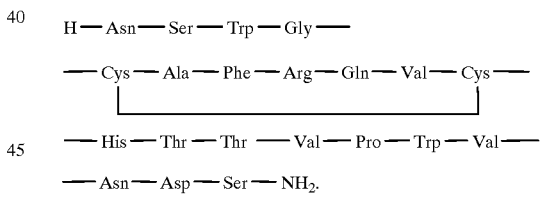

18. A diagnostic immunoassay kit according to claim 17, characterized in that it additionally comprises a positive standard serum sample, a negative standard serum sample, an enzyme conjugate, optionally a substrate for the enzyme conjugate, and optionally buffer solution(s) and/or washing solution(s).

19. A diagnostic immunoassay kit according to claim 17, wherein said peptide has been immobilized or coupled to a carrier.

20. An isolated and purified peptide having a sulfur bridge between two cysteine residues formed by a chemical oxidation step, of formula:

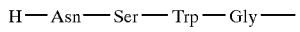

-continued

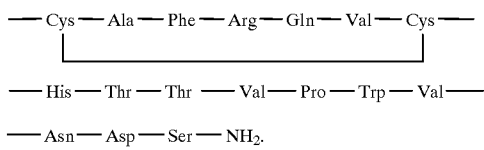

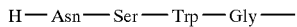

—Asn—Asp—Ser—NH$_2$.

21. An antigen which specifically binds with antibodies induced by a HIV characterized in that the antigen was produced with an isolated and purified peptide having a sulfur bridge between two cysteine residues formed by a chemical oxidation step, of formula:

H—Asn—Ser—Trp—Gly—

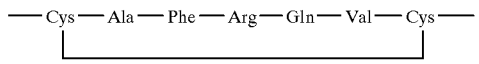

-continued

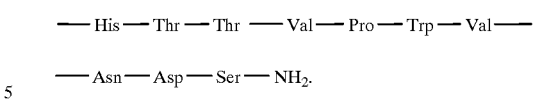

—Asn—Asp—Ser—NH$_2$.

22. An antigen according to claim 21, characterized in that it has been immobilized or coupled to a carrier.

23. A method of detecting antibodies induced by a HIV in a sample of body fluid, wherein said sample is subjected to an immunoassay, characterized in that an antigen according to claim 20 is used as a diagnostic antigen.

24. A method according to claim 23, wherein said sample is subjected to enzyme-linked immunosorbant assay (ELISA) characterized in that said artificial antigen is used as a diagnostic coating antigen.

* * * * *

UNITED STATES PATENT AND TRADEMARK OFFICE
CERTIFICATE OF CORRECTION

PATENT NO. : 5,981,170  
DATED : November 9, 1999  
INVENTOR(S) : Jerzy Trojnar et al.

Page 1 of 1

It is certified that error appears in the above-identified patent and that said Letters Patent is hereby corrected as shown below:

Title page,  
"[73] Assignee: Ferring AB" should read -- [73] Assignee: EuroDiagnostica AB --.

Column 1,  
Line 34, "characterised" should read -- characterized --.

Column 7,  
Line 1, "Gln" to should -- Glu --.

Column 9,  
Line 40, "fluorid" should read -- fluoride --.

Column 11,  
Line 42, and 43, "HIV-2-gp41" should read -- HIV-transmembrane --.

Column 15,  
Line 45, "H-Gly-Ile-Trp-Gly-Cys-Ser-Gly-Lys-Leu-Ili-Cys-Thr-Th" should read  
-- H-Gly-Ile-Trp-Gly-Cys-Ser-Gly-Lys-Leu-Ili-Cys-Thr-Thr --.

Signed and Sealed this

Eleventh Day of September, 2001

*Attest:*

NICHOLAS P. GODICI  
*Attesting Officer*     *Acting Director of the United States Patent and Trademark Office*